US 8,814,835 B2

(12) United States Patent
Baid

(10) Patent No.: US 8,814,835 B2
(45) Date of Patent: Aug. 26, 2014

(54) NEEDLE GUARDS AND INTRAVENOUS CATHETER APPARATUS COMPRISING THE NEEDLE GUARDS

(75) Inventor: Rishi Baid, New Delhi (IN)

(73) Assignee: Poly Medicure Limited, Faridabad, Haryana (IN)

( * ) Notice: Subject to any disclaimer, the term of this patent is extended or adjusted under 35 U.S.C. 154(b) by 274 days.

(21) Appl. No.: 13/351,870

(22) Filed: Jan. 17, 2012

(65) Prior Publication Data

US 2013/0018330 A1 Jan. 17, 2013

(30) Foreign Application Priority Data

Jan. 17, 2011 (IN) .............................. 105/DEL/2011

(51) Int. Cl.
*A61M 5/00* (2006.01)
(52) U.S. Cl.
USPC ........................ 604/263; 604/110; 604/164.08
(58) Field of Classification Search
CPC ..................... A61M 25/0631; A61M 25/0618; A61M 25/0625; A61M 25/0612; A61M 5/3213; A61M 5/3273; A61M 2005/3247; A61M 2005/3249; A61M 2005/325
USPC ............ 604/263, 164.08, 110, 192, 162, 198, 604/199
See application file for complete search history.

(56) References Cited

U.S. PATENT DOCUMENTS

| 6,749,588 B1 * | 6/2004 | Howell et al. ............ 604/164.08 |
| 7,264,613 B2 * | 9/2007 | Woehr et al. ............. 604/164.08 |
| 7,374,554 B2 * | 5/2008 | Menzi et al. .................. 604/110 |
| 2001/0039401 A1 | 11/2001 | Ferguson et al. |
| 2002/0103463 A1 | 8/2002 | Luther et al. |
| 2008/0051724 A1 | 2/2008 | Bedford et al. |

OTHER PUBLICATIONS

European Patent Office Search Report mailed Mar. 23, 2012 in reference to co-pending European Patent Application No. 12151145.5-2320.

* cited by examiner

*Primary Examiner* — Bhisma Mehta
*Assistant Examiner* — Nicholas Meghri
(74) *Attorney, Agent, or Firm* — Dinsmore & Shohl, LLP

(57) ABSTRACT

A needle guard may include a base portion having a hole adapted to accommodate a needle shaft of a needle such that the needle may extend through the hole and move relative to the needle guard from a ready position in which the needle tip is outside the needle guard to a protective position in which the needle tip is covered by the needle guard. Arms of the needle guard may extend distally from the base portion generally in an axial direction. The arms may comprise sections bent to define a passage for the needle in the needle guard. An intravenous catheter apparatus may include the needle guard in combination with a needle and a catheter tube attached to a catheter hub, the catheter hub having a chamber. The needle guard may be slidably arranged on the needle shaft and housed in the chamber of the catheter hub.

19 Claims, 3 Drawing Sheets

NEEDLE GUARDS AND INTRAVENOUS CATHETER APPARATUS COMPRISING THE NEEDLE GUARDS

CROSS-REFERENCES TO RELATED APPLICATIONS

This application claims the benefit of priority under 35 U.S.C. §119(a)-(d) to Indian Patent Application No. 105/DEL/2011, filed Jan. 17, 2011.

TECHNICAL FIELD

The present invention relates generally to medical apparatus and, more particularly, to safety devices for medical apparatus such as needles.

BACKGROUND

It is well known that blood-borne diseases such as AIDS and hepatitis present significant risks to health-care workers administering vascular injections. Accidental needle sticks or needle pricks have become a major concern to health-care workers. The chances of needle stick increase during an emergency with several aspects required to be handled. Likewise, during disposal, an exposed needle tip may be and usually is a threat to the medical-waste handler.

To adequately protect health-care workers from inadvertent needle sticks and wounding, safety catheter assemblies have been developed to automatically cover and shield the needle tip after its withdrawal from the patient. These assemblies have taken a number of forms and have various degrees of elaboration. However, the safety mechanisms implemented in these assemblies increase costs of manufacture substantially and may malfunction, especially in a fluid-filled environment where they may stick or slip. Some of the known needle-protecting systems require multiple parts, which drives up the manufacturing cost for a disposable unit.

The cost-benefit requirements of the medical industry call for an inexpensive needle protecting system that is disposable along with the needle. Furthermore, the system must be quick and easy to use as to present as little imposition as possible to the administration and function of the safety IV catheter assembly.

Therefore, there are ongoing needs for protective systems that are simple and dependable in their deployment, inexpensive to manufacture, expedient in their operation, effective in protecting a needle tip, and that ensure correct functioning even after longer shelf life.

SUMMARY

Embodiments described herein are directed to needle guards for a needle, such as a hypodermic needle, for example. The needle guard may be incorporated into larger medical apparatus, such as a safety intravenous catheter apparatus, for example. The needle guard includes a base portion having a hole, the dimension of which is adapted to a needle shaft of the needle such that the needle may extend through the hole and move relative to the needle guard. In particular, the needle may be moved from a ready position in which the needle tip is outside the needle guard to a protective position in which the needle tip is covered by the needle guard. The needle guard further includes first and second arms extending distally from the base portion.

Further embodiments described herein are directed to intravenous catheter apparatus including the needle guard.

According to some embodiments, the intravenous catheter apparatus may include a catheter tube, a catheter hub, a needle, and a needle guard according to one or more embodiments described herein. The catheter hub may be attached to a proximal end of the catheter tube and may have a wall defining a chamber. The needle guard may be slidably arranged on the needle shaft and housed in the chamber of the catheter hub.

The following description and the appended claims will describe additional embodiments of the needle guards and the intravenous catheter apparatus including the needle guards.

BRIEF DESCRIPTION OF THE DRAWINGS

Certain non-limiting embodiments are illustrated in detail through the accompanying drawings, in which.

DETAILED DESCRIPTION

Features and advantages of the invention will now be described with occasional reference to specific embodiments. It should be understood that the specific embodiments are provided for illustrative purposes and are not meant to limit the scope of the appended claims. However, the invention may be embodied in different forms and should not be construed as limited to the embodiments set forth herein. Rather, these embodiments are provided so that this disclosure will be thorough and complete and will fully convey the scope of the invention to those skilled in the art.

According to some embodiments, a needle guard includes a base portion having a hole the dimension of which is adapted to the needle shaft such that the needle may extend through the hole and move relative to the needle guard from a ready position in which the needle tip is outside the needle guard to a protective position in which the needle tip is covered by the needle guard. The needle guard further may include first and second arms extending from a distal side of the base portion generally in the axial direction, wherein each of the first and second arms has a main portion and a distal end portion. The main portion of the second arm may include two outer arm sections and an inner arm section, wherein the inner arm section is bent away from the first arm and the outer arm sections are bent toward the first arm, thereby defining a passage for the needle, which is axially aligned with the hole in the base portion. Thereby, the inner and outer arm sections may create a "three leg formation" composed of two legs substantially parallel to each other and extending radially inwardly toward the first arm and further composed of one leg extending radially outwardly in an opposing manner.

As used herein, the term "proximal" refers to a region of the device or a location on the device which is closest to a clinician using the device, for example. As used herein, the term "distal" refers to a region of the device that is farthest from the clinician, for example, and generally is opposite the proximal region. In the context of the needle guides described herein, the distal region of a needle will be the region of a needle containing the needle tip which is to be inserted into a patient's vein, for example. As a further illustration, the distal end of a needle (i.e., the needle tip) may be inserted into the proximal end of a device, such that, when fully inserted into the device, the distal end of the needle reaches the distal end of the device.

An embodiment of a needle guard will be described now with reference to FIGS. 1-4. These figures illustrate a needle guard 10 for a needle 12, such as a hypodermic needle, for example. The needle 12 may itself be a component of a medical apparatus, such as an intravenous catheter apparatus, for example. Embodiments of intravenous catheter apparatus will be described below with reference to FIGS. 5 and 6.

Figure 1:
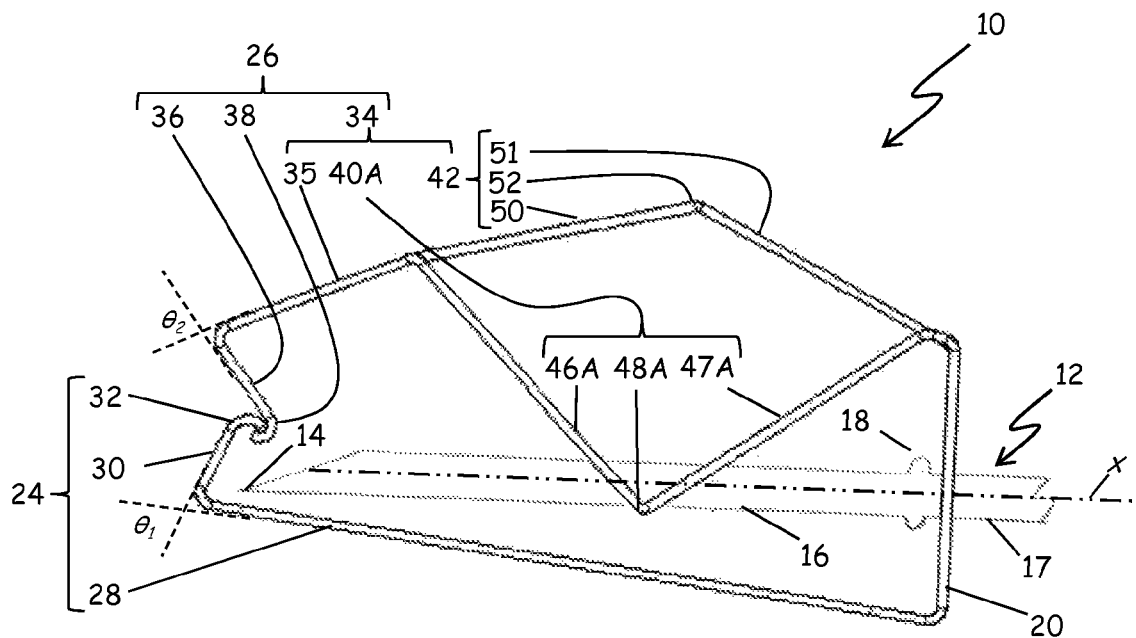
FIG. 1 is a side view of a needle guard according to embodiments described herein, shown in a protective position.

As shown in FIG. 1, the needle 12 has a needle tip 14 and a needle shaft 16. The needle shaft 16 has a principal outer profile and defines an axial direction x. In some embodiments, near the needle tip 14 the needle 12 may be provided with an enlargement 18, a maximum outer dimension of which is greater than the principal outer profile of the needle shaft 16. The enlargement 18 can be formed, for example, by crimping of the needle shaft 16. However, it is also possible to form the enlargement 18 by adding additional material to the needle shaft 16, for instance, by welding, soldering or gluing.

In some embodiments, it may be preferable that the needle guard 10 is an integral, stamped, and bent part made of a sheet material having elastic properties. The needle guard 10 is particularly easy and inexpensive to manufacture, if the needle guard 10 is an integral stamped and bent part. Preferably, the needle guard 10 may comprise a material having elastic properties. For example, the needle guard 10 can be made of a sheet material, in particular, a metal sheet, such as a stainless steel sheet. However, it should be understood that other flexible strong materials could also be used to form the needle guard 10. Because of the elastic properties of the material, the needle guard 10 can be easily designed such that its arms snap together when the needle 12 adopts its protective position, as described below. Consequently, there is no need for an additional part that provides a restoring force, such as an elastic band surrounding the arms.

Figure 2:
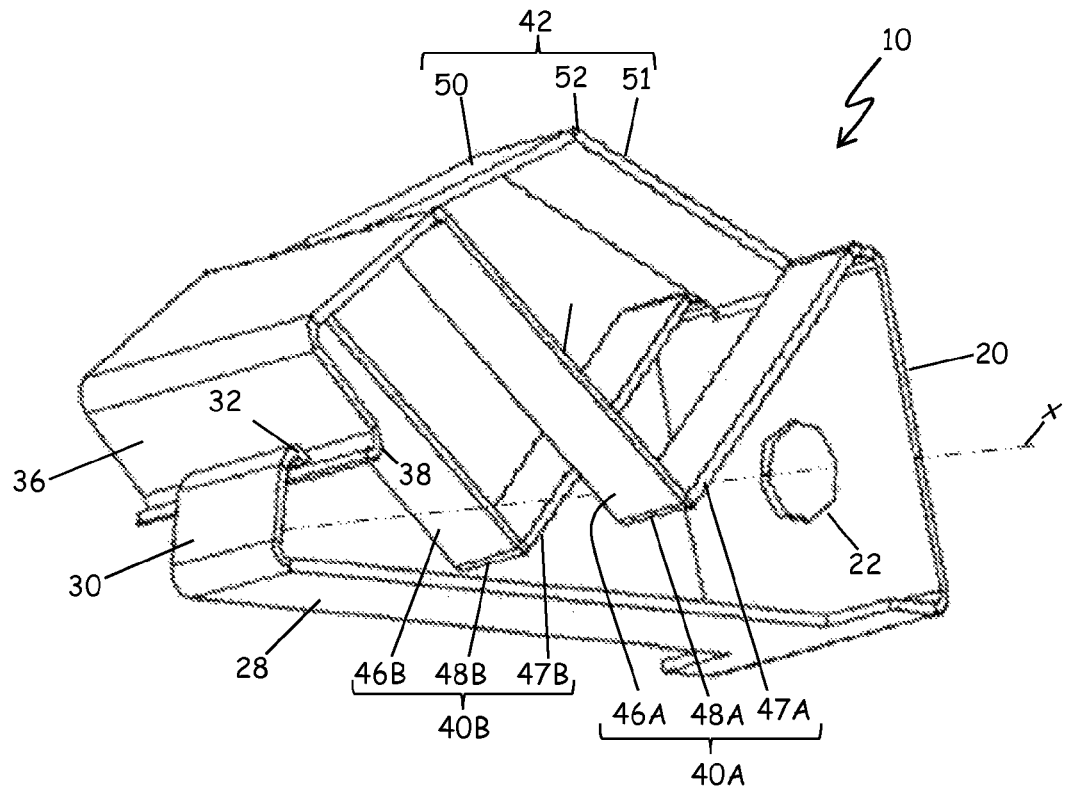
FIG. 2 is a perspective view of the needle guard of FIG. 1.
Figure 3:
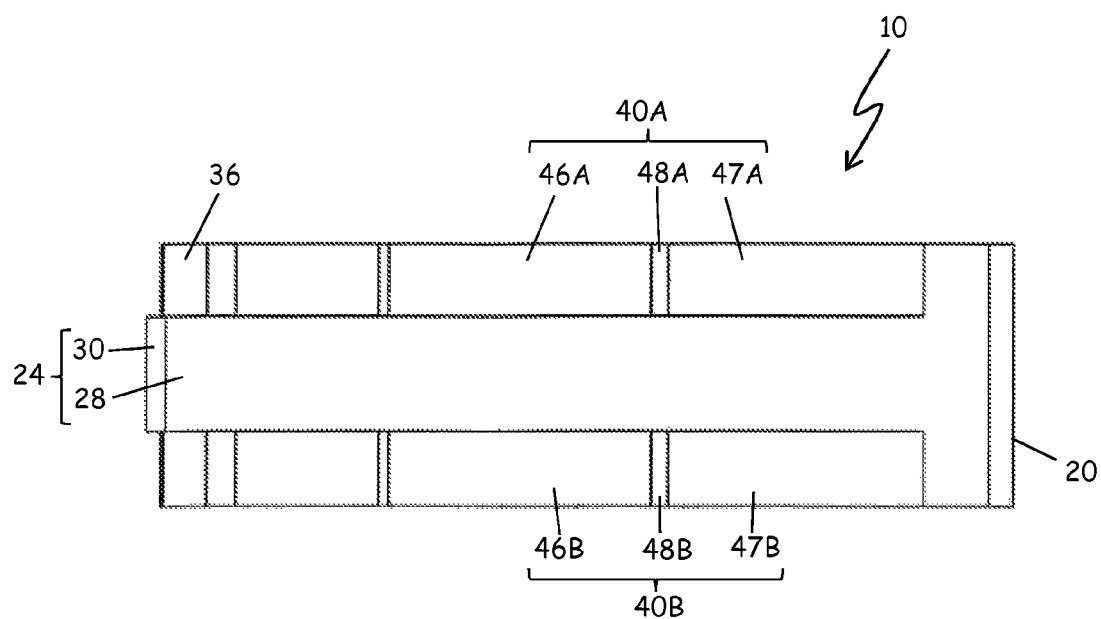
FIG. 3 is a bottom view of the needle guard of FIG. 1.

Referring to FIGS. 1 and 2, the needle guard 10 comprises a base portion 20 which is provided with a hole 22. The shape of the hole 22 is adapted to the principal outer profile of the needle shaft 16, such that a proximal portion 17 of the needle shaft 16 proximal from the enlargement 18 can extend through the hole 22 and the needle 12 can move relative to the needle guard 10 from a ready position (not shown in FIG. 1, but illustrated in FIG. 5 with respect to an intravenous catheter apparatus described below) in which the needle 12 extends all the way through the needle guard 10 and the needle tip 14 is outside the needle guard 10, to a protective position in which the needle tip 14 is covered by the needle guard 10, as shown in FIG. 1.

A maximum dimension of the hole 22 is smaller than the maximum outer dimension of the enlargement 18, such that the enlargement 18 cannot pass through the hole 22 and the needle guard 10 is prevented from sliding off the needle 12 beyond the needle tip 14. The hole 22 is not necessarily limited to any particular shape such as a circle, for example, provided the enlargement 18 cannot pass through the hole 22.

The needle guard 10 further comprises a first arm 24 and a second arm 26, both of which extend distally from the base portion 20, generally in the axial direction x, on opposite sides of the needle 12. In this sense, "generally in the axial direction x" means that the first arm 24 and the second arm 26 are configured such that the needle 12 may be inserted between the first arm 24 and the second arm 26 without protruding from a side of the needle guard 10. Though in some embodiments the first arm 24 and the second arm 26 are substantially parallel, this is not a requirement.

According to some embodiments, the distal end portions 30, 36 of the first and second arms 24, 26 extend toward each other. The distal end portions 30, 36 thus form transverse walls that prevent the needle tip 14 received in the needle guard 10 from protruding from the needle guard 10 at the distal end of the needle guard 10 opposite the base portion 20.

According to further embodiments, the distal end portions 30, 36 of the first and second arms 24, 26 form an acute angle with the main portions 28, 34 of the arms 24, 26. In other words, the distal end portions 30, 36 of the arms 24, 26 are bent backwards, i.e. toward the base portion 20.

Preferably, free end regions 32, 38 of each distal end portion 30, 36 is formed in a hook-like manner such that the distal end portions 30, 36 of the first and second arms 24, 26 lock when the needle 12 adopts its protective position, as shown in FIG. 1. The needle tip 14 received in the needle guard 10 is thus safely captured inside the needle guard 10 and cannot protrude from the needle guard 10 at the distal end thereof.

The locking of the first and second arms 24, 26 can be achieved, for example, if the free end region 32 of the one distal end portion 30, e.g. of the first arm 24, is bent toward the base portion 20 and the free end region 38 of the other distal end portion 36, e.g. of the second arm 26, is bent away from the base portion 20. It should be understood that this configuration is provided as illustrative only and that other manners and configurations of locking the first and second arms 24, 26 may be made.

According to a further embodiment, the first and second arms 24, 26 may be biased toward each other such that the first and second arms 24, 26 are spread apart against a restoring force by the distal end portions 30, 36 being supported on the needle shaft 16 when the needle 12 is in its ready position (see FIG. 5), and snap together when the needle 12 adopts its protective position (see FIG. 6) and the distal end portions 30, 36 move in front of the needle tip 14.

The above embodiments are further described with reference to FIG. 1. As shown in FIG. 1, the first arm 24 has a main portion 28 that is generally straight and a distal end portion 30 that is bent toward the second arm 26. In some embodiments, the main portion 28 of the first arm 24 forms an acute angle ($\theta_1 < 90°$) with the distal end portion 30 of the first arm 24, i.e. the distal end portion 30 is bent slightly backwards (i.e., in the proximal direction) toward the base portion 20. In some embodiments, a free end region 32 of the distal end portion 30 of the first arm 24 may be bent in a hook-like configuration. As shown in FIG. 1, the hook-like configuration may be oriented back toward the base portion 20 at the proximal side of the needle guide 10.

The second arm 26 also has a main portion 34 and a distal end portion 36. The distal end portion 36 of the second arm 26 is bent toward the first arm 24. The distal end portion 36 of the second arm further may be bent toward and the base portion 20, such that the distal end portion 36 of the second arm 26 forms an acute angle ($\theta_2 < 90°$) with the main portion 34 of the second arm 26. A free end region 38 of the distal end portion 36 of the second arm 26 may be bent in a hook-like manner away from the base portion 20.

Figure 5:
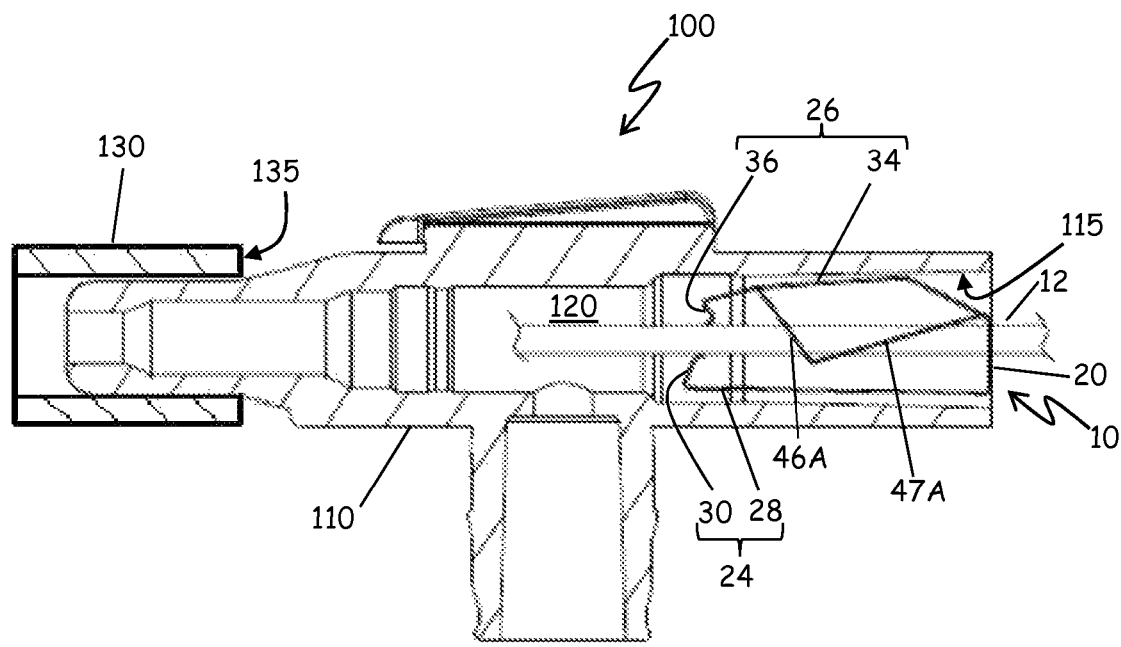
FIG. 5 is a plan view of an intravenous catheter apparatus according to embodiments described herein, including the needle guard of FIG. 1 in a protective position.

The ready position is described now with reference to FIG. 1 and to only the needle guard 10 depicted in FIG. 5. When the needle 12 is in its ready position (as shown in FIG. 5) the first and second arms 24, 26 are spread apart against a restoring force, such that the distal end portions 30, 36 of each arm are supported on the needle shaft 16. When the needle 12 is moved toward its protective position and the needle tip 14 passes the distal end portions 30, 36, the first and second arms 24, 26 snap together and the free end regions 32, 38 engage with each other to lock the first and second arms 24, 26, as shown in FIGS. 1 and 2 (showing the protective position). In this state, the distal end portions 30, 36 form in combination a transverse wall in front of the needle tip 14 that prevents the needle tip 14 from distally projecting out of the needle guard 10 as was possible in the ready position described above with reference to FIG. 5. At the same time, the enlargement 18 engages with the base portion 20, thereby preventing the needle guard 10 from sliding off the needle 12 in the distal direction (i.e., such that the needle tip 14 would slide back through the hole 22).

According to some embodiments, arm sections of the second arm 26 are defined by two parallel cuts in the second arm 26. Thereby, the needle guard 10 is particularly easy to manufacture. If the arm sections are to terminate at the base portion, the two cuts preferably also terminate at the base portion. To obtain a sufficient width of the needle passage, the cuts are preferably spaced apart by a distance equal to or slightly larger than the principal diameter of the needle shaft.

Figure 4:
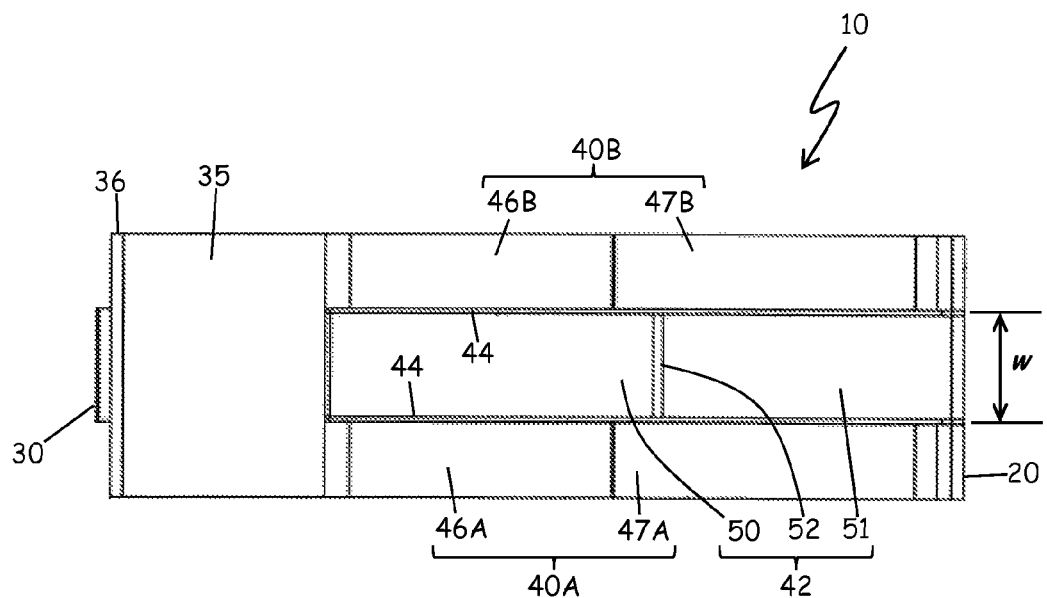
FIG. 4 is a top view of the needle guard of FIG. 1.

The cuts are illustrated now referring to FIGS. 1-4. In particular, the main portion 34 of the second arm 26 includes two outer arm sections 40A, 40B and an inner arm section 42. As shown in FIG. 4, which depicts a top view of the needle guard 10 and shows details of the second arm 26 (see also FIG. 1), the outer and inner arm sections 40A, 40B, 42 are defined by two cuts 44 in the second arm 26, which extend parallel to one another in the axial direction from an uncut portion 35 of the second arm 26 to the base portion 20 (FIG. 4). The distance w between the cuts 44 may be equal to or slightly larger than (for example, from 5% to 10% larger than) the width of the needle shaft 16.

According to further embodiments, each of the outer arm sections comprises two subsections extending at an angle, the vertex of which points toward the first arm. Similarly, the inner arm section comprises two subsections extending at an angle, the vertex of which points away from the first arm. The two subsections of each outer arm section thus form a V-shape, whereas the subsections of the inner arm section form an inverted V-shape. The V-like shape of the outer and inner arm sections facilitates the flexing of the arms to and from a biased condition. However, it should be understood that the subsections of the inner and outer arm sections do not necessarily need to extend at sharp angles. It also possible, that the subsections of each arm section are connected to each other by a curved or bent portion defining a certain radius.

According to a further embodiment, a proximal end of each of the arm sections terminates at the base portion. Alternatively, it would be possible to provide an intermediate portion between the arm sections and the base portion, which extends generally in the axial direction.

As illustrated in the embodiment shown in FIGS. 1-4, each of the outer arm sections 40A, 40B comprises two subsections. Outer arm section 40A comprises subsections 46A and 47A, and outer arm section 40B comprises subsections 46B and 47B. Referring to FIG. 2 for illustration, subsections 46A and 47A of the outer arm section 40A are angled toward the first arm 24, such that the vertex 48A of the angle points toward the first arm 24. Likewise, subsections 46B and 47B of outer arm section 40B are angled toward the first arm 24, such that the vertex 48B of the angle points toward the first arm 24

The outer arm sections 40A, 40B are bent so as to define a passage for the needle 12 between them. The passage is axially aligned with the hole 22 in the base portion 20 and, thus, prevents the needle tip 14 from protruding sideways from the needle guard 10. The general pathway of the passage may be discerned from FIG. 2, for example, from the path of the axial direction x.

The inner arm section 42 comprises two subsections 50, 51 that extend at an angle away from the first arm 24, such that the vertex 52 of the angle points away from the first arm 24.

In the spread apart state of the first arm 24 and the second arm 26 (see FIG. 5), the inner arm section 42 is bent, and the vertex 52 of the bent inner arm section 42 can engage with a wall of a catheter hub to retain the needle guard 10 inside the catheter hub as long as the needle tip 14 is not yet received and protected by the needle guard 10. This configuration will be described now with reference to embodiments of intravenous catheter apparatus.

A needle guard according to any of the embodiments described above can be used in a larger apparatus such as an intravenous catheter apparatus, for example. A non-limiting embodiment of an intravenous catheter apparatus 100 is shown in FIGS. 5 and 6, though features of the needle guard 10 therein may be mentioned with reference to any or all of FIGS. 1-4.

Figure 6:
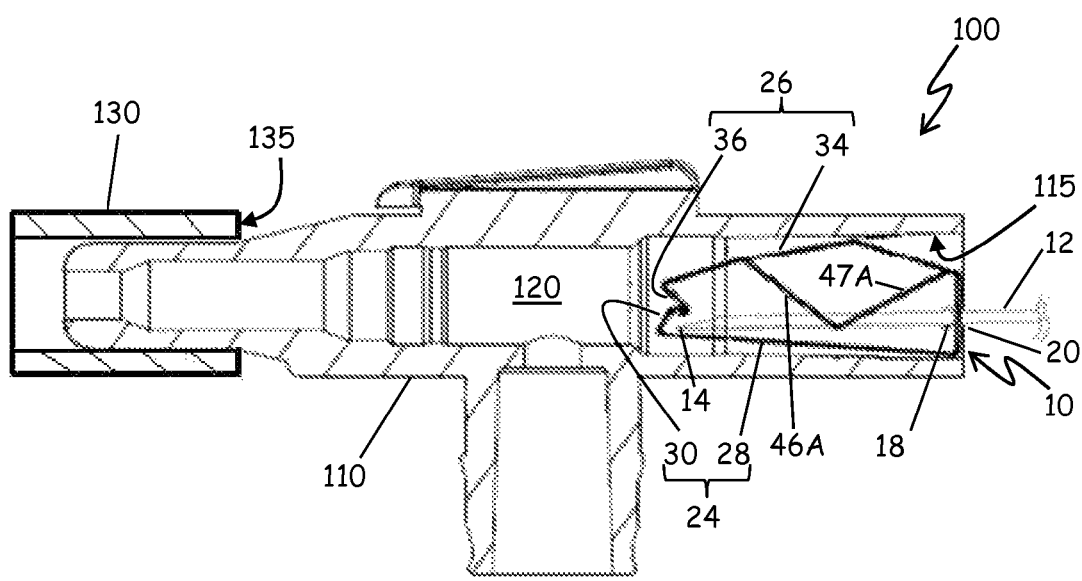
FIG. 6 is a plan view of the intravenous catheter apparatus of FIG. 5, in which the needle guard is in a ready position.

Referring to FIGS. 1, 5, and 6, according to some embodiments, an intravenous catheter apparatus 100 may include a catheter tube 130, a catheter hub 110 attached to a proximal end 135 of the catheter tube 130 and having a wall 115 defining a chamber 120, and a needle 12 having a needle tip 14 and a needle shaft 16. The intravenous catheter apparatus 100 further includes a needle guard 10 in accordance with one or more of the embodiments described above. The needle guard 10 is slidably arranged on the needle shaft 16 and housed in the chamber 120 of the catheter hub 110.

According to some embodiments, the needle shaft 16 includes an enlargement 18 near the needle tip 14, a dimension of which is greater than the maximum hole dimension of the hole 22 (see FIG. 2) in the base portion 20 of the needle guard 10. The enlargement 18 can be made by crimping of the needle shaft 16. However, other ways of forming the enlargement 18 are possible, such as applying additional material to the needle shaft 16 by soldering, welding, or gluing, for example. The inner profile of the needle can either be reduced in the region of the enlargement 18, for example, if the enlargement is formed by crimping, or it can be substantially constant throughout the length of the needle 12, for example, if the enlargement 18 is formed by applying additional material to the needle shaft 16.

Referring to FIGS. 1, 2, and 5, according to a further embodiment, the main portion 34 of the second arm 26 of the needle guard 10 engages with the wall 115 of the catheter hub 110 when the needle 12 is in its ready position, thereby retaining the needle guard 10 in the catheter hub 110. Referring to FIGS. 1, 2, and 6, the main portion 34 of the second arm 26 of the needle guard 10 is disengaged from the wall 115 of the catheter hub 110 when the needle 12 is in its protective position, thereby allowing removal of the needle guard 10 from the catheter hub 110.

Prior to use, a needle guard 10 according to embodiments described herein may be arranged in a chamber 120 of a medical device, for example in the catheter hub 110 of an intravenous catheter apparatus 100, and may be positioned near a proximal end of the needle shaft 16. In this situation, the needle 12 extends completely through the needle guard 10, thereby supporting the distal end portions 30, 36 of the first and second arms 24, 26 on the needle shaft 16 and deflecting the first and second arms 24, 26 of the needle guard 10 outwards. In this deflected state, the main portion 34 of the second arm 26 of the needle guard 10 can engage with the wall 115 of the catheter hub 110 to retain the needle guard 10 therein.

Following the insertion of the catheter tube 130 into a patient, the needle 12 may be withdrawn from the catheter tube 130 and the needle shaft 16 moves through the needle guard 10 while the needle guard 10 is retained in the catheter hub 110. Once the needle tip 14 passes the distal end of the needle guard 10, such that the needle shaft 16 no longer supports the distal end portions 30, 36 of the arms 24, 26, a restoring force ensures that the arms 24, 26 of the needle guard 10 are moved back into alignment with the axial direction of the needle guard 10, so that the needle tip 14 is blocked by the distal end portions 30, 36 of the arms 24, 26. Thereby, the needle tip 14 is prevented from axially projecting out of the needle guard 10.

Because of the bent shape of the outer arm subsections 46A, 46B, 47A, 47B, and the needle passage defined thereby, axial alignment of the needle guard 10 with the needle 12 is ensured at all times, i.e. the needle tip 14 is prevented from protruding sideways from the needle guard 10 when the needle 12 has moved to its protective position. It is to be understood that the width of the inner arm section 42 is substantially equal to or slightly larger than the principal outer profile of the needle shaft 16, such that the needle 12 is allowed to pass through the needle passage.

By moving back into alignment with the axial direction, the main portion 34 of the second arm 26 of the needle guard 10 can disengage from the 115 wall of the catheter hub 110. In addition, an enlargement 18 of the needle shaft 16 can engage with the base portion 20 to allow removal of the needle guard 10 from the catheter hub 110 and to prevent the needle guard 10 from sliding off the distal end of the needle shaft 16.

Though the invention has been described in detail and by reference to specific embodiments, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A needle guard for a needle having a needle tip and a needle shaft that defines an axial direction, the needle guard comprising:
    a base portion defining a proximal end of the needle guard;
    a first arm; and
    a second arm,
    wherein:
        the base portion has a hole defined therein, the hole having a hole dimension adapted to the needle shaft such that the needle is insertable through the hole and moveable relative to the needle guard from a ready position to a protective position, whereby:
            in the ready position, the needle extends all the way through the needle guard and the needle tip of the needle is outside the needle guard; and
            in the protective position, the needle tip of the needle is covered by the needle guard and the needle tip does not protrude from the needle guard at a distal end of the needle guard opposite the proximal end of the needle guard;
        the first arm and the second arm each extend generally in the axial direction from a distal side of the base portion;
        the first arm and the second arm each comprise a main portion and a distal end portion;
        the main portion of the second arm comprises two outer arm sections and an inner arm section;
        the inner arm section of the main portion of the second arm is bent away from the first arm;
        the two outer arm sections of the main portion of the second arm both are bent toward the first arm;
        a passage for accommodating the needle is defined between the two outer arm sections;
        the passage is axially aligned with the hole in the base portion; and
        the arm sections are defined by two parallel cuts in the second arm that terminate at the base portion.

2. The needle guard of claim 1, wherein only each of the outer arm sections, only the inner arm section, or each of the outer arm sections and the inner arm section comprises two subsections, the two subsections of each outer arm section meeting at an angle having an outer-arm vertex that points toward the first arm, the two subsections of the inner arm section meeting at an angle having an inner-arm vertex that points away from the first arm.

3. The needle guard of claim 1, wherein a proximal end of each of the arm sections terminates at the base portion.

4. The needle guard of claim 1, wherein the distal end portions of the first and second arms extend toward each other.

5. The needle guard of claim 1, wherein the distal end portions each form an acute angle with their respective main portion.

6. The needle guard of claim 1, wherein a free end region of each distal end portion is formed in a hook-like manner such that the distal end portions of the first and second arms lock when the needle is in the protective position.

7. The needle guard of claim 1, wherein a free end region of the distal end portion of one of the first or second arm is bent toward the base portion and a free end region of the distal end portion of the other of the first or second arm is bent away from the base portion.

8. The needle guard of claim 1, wherein:
    in the ready position the first and second arms are biased toward each other such that the first and second arms are spread apart against a restoring force, and the distal end portions are supported on the needle shaft; and
    in the protective position, the first and second arms snap together and the distal end portions move in front of the needle tip.

9. The needle guard of claim 1, wherein the needle guard is an integral stamped and bent part.

10. The needle guard of claim 1, wherein the needle guard comprises a material having elastic properties.

11. The needle guard of claim 1, wherein the needle guard is made of a sheet material.

12. The needle guard of claim 1, wherein the needle guard is made of a stainless steel sheet.

13. An intravenous catheter apparatus comprising:
    a catheter tube;
    a catheter hub attached to a proximal end of the catheter tube and having a wall defining a chamber;
    a needle having a needle tip, a needle shaft, and a proximal end opposite the needle tip; and
    a needle guard according to claim 1, which is slidably arranged on the needle shaft and is housed in the chamber of the catheter hub.

14. The intravenous catheter apparatus of claim 13, wherein the needle shaft includes an enlargement between the needle tip and the proximal end of the needle, the enlargement having an enlargement dimension greater than the hole dimension of the hole in the base portion of the needle guard.

15. The intravenous catheter apparatus of claim 13, wherein the main portion of the second arm of the needle guard is engaged with the wall of the catheter hub when the needle is in its ready position and disengaged from the wall when the needle is in its protective position.

16. A needle guard for a needle having a needle tip and a needle shaft that defines an axial direction, the needle guard comprising:
- a base portion defining a proximal end of the needle guard;
- a first arm; and
- a second arm, wherein:
- the base portion has a hole defined therein, the hole having a hole dimension adapted to the needle shaft such that the needle is insertable through the hole and moveable relative to the needle guard from a ready position to a protective position, whereby:
  - in the ready position, the needle extends all the way through the needle guard and the needle tip of the needle is outside the needle guard; and
  - in the protective position, the needle tip of the needle is covered by the needle guard and the needle tip does not protrude from the needle guard at a distal end of the needle guard opposite the proximal end of the needle guard;
- the first arm and the second arm each extend generally in the axial direction from a distal side of the base portion;
- the first arm and the second arm each comprise a main portion and a distal end portion;
- the main portion of the second arm comprises two outer arm sections and an inner arm section;
- the inner arm section of the main portion of the second arm is bent away from the first arm;
- the two outer arm sections of the main portion of the second arm both are bent toward the first arm;
- a passage for accommodating the needle is defined between the two outer arm sections;
- the passage is axially aligned with the hole in the base portion; and
- a proximal end of each of the arm sections terminates at the base portion.

17. The needle guard of claim 16, wherein the arm sections are defined by two parallel cuts in the second arm that terminate at the base portion.

18. The needle guard of claim 16, wherein a free end region of each distal end portion is formed in a hook-like manner such that the distal end portions of the first and second arms lock when the needle is in the protective position.

19. The needle guard of claim 16, wherein a free end region of the distal end portion of one of the first or second arm is bent toward the base portion and a free end region of the distal end portion of the other of the first or second arm is bent away from the base portion.

* * * * *